United States Patent
Akbari et al.

(10) Patent No.: US 12,194,280 B2
(45) Date of Patent: Jan. 14, 2025

(54) DRUG DELIVERY DEVICES AND ASSOCIATED HEATING AND/OR COOLING DEVICES

(71) Applicant: AMGEN INC., Thousand Oaks, CA (US)

(72) Inventors: Samin Akbari, Cambridge, MA (US); Tohid Pirbodaghi, Cambridge, MA (US); Sheldon B. Moberg, Thousand Oaks, CA (US)

(73) Assignee: AMGEN INC., Thousand Oaks, CA (US)

( * ) Notice: Subject to any disclaimer, the term of this patent is extended or adjusted under 35 U.S.C. 154(b) by 919 days.

(21) Appl. No.: 17/196,744

(22) Filed: Mar. 9, 2021

(65) Prior Publication Data

US 2021/0316075 A1    Oct. 14, 2021

Related U.S. Application Data

(60) Provisional application No. 63/009,226, filed on Apr. 13, 2020.

(51) Int. Cl.
*A61M 5/24* (2006.01)
*A61M 5/32* (2006.01)

(52) U.S. Cl.
CPC .............. *A61M 5/24* (2013.01); *A61M 5/32* (2013.01); *A61M 2202/064* (2013.01); *A61M 2205/02* (2013.01); *A61M 2205/36* (2013.01)

(58) Field of Classification Search
CPC ....... A61M 5/24; A61M 5/32; A61M 5/14248
See application file for complete search history.

(56) References Cited

U.S. PATENT DOCUMENTS

| | | | | |
|---|---|---|---|---|
| 8,715,232 | B2 * | 5/2014 | Yodfat | A61M 5/14248 604/164.12 |
| 9,333,144 | B2 | 5/2016 | Baxter et al. | |
| 9,808,577 | B2 | 11/2017 | Nagar et al. | |
| 10,149,641 | B2 | 12/2018 | O'Malley et al. | |
| 10,920,346 | B2 * | 2/2021 | Reneker | D01F 1/10 |
| 2006/0135911 | A1 | 6/2006 | Mittur | |
| 2016/0045678 | A1 | 2/2016 | Vallero et al. | |
| 2017/0043101 | A1 * | 2/2017 | Cole | A61M 25/0631 |
| 2017/0224935 | A1 * | 8/2017 | Hoffmann | A61M 5/24 |
| 2020/0316290 | A1 * | 10/2020 | Bourelle | A61M 5/31 |
| 2021/0353222 | A1 * | 11/2021 | Hooven | A61B 5/6833 |

FOREIGN PATENT DOCUMENTS

WO    WO-2018/170176 A1    9/2018

* cited by examiner

*Primary Examiner* — Dung T Ulsh
(74) *Attorney, Agent, or Firm* — MARSHALL, GERSTEIN & BORUN LLP; Michael P. Furmanek

(57) ABSTRACT

Drug delivery devices and associated heating and/or cooling devices are disclosed. In an example, a drug delivery device includes a housing, a container, a therapy layer, and a first adhesive layer. The housing includes a top wall and a bottom wall. The container is at least partially disposed within the housing. The container has an inner volume to contain a drug. The therapy layer have a first side and a second side. The first side faces the bottom wall and the second side faces away from the bottom wall. The first adhesive layer couples the first side of the therapy layer and the bottom wall. The therapy layer is adapted to at least one of heat or cool an area adjacent an injection site.

20 Claims, 3 Drawing Sheets

DRUG DELIVERY DEVICES AND ASSOCIATED HEATING AND/OR COOLING DEVICES

CROSS-REFERENCE TO RELATED APPLICATION

The priority benefit of U.S. Provisional Patent Application No. 63/009,226, filed on Apr. 13, 2020, is hereby claimed and the entire contents thereof are incorporated herein by reference.

FIELD OF DISCLOSURE

The present disclosure generally relates to drug delivery devices and more particularly, but not necessarily exclusively, heating or cooling an injection site during a drug delivery process using such drug delivery devices.

BACKGROUND

Drug delivery devices, such as injectors, are used to deliver liquid drugs to a patient. Upon activation, a drug delivery device will expel a drug stored within an internal reservoir through a needle, cannula, or other delivery member into the patient during what may be referred to as a drug delivery process. However, because of the nature of the drug delivery process and/or the drug delivered to the patient, the drug delivery process be may uncomfortable or painful for some patients.

The present disclosure sets forth drug delivery devices embodying advantageous alternatives to existing drug delivery devices, and that may address one or more of the challenges or needs mentioned herein, as well as provide other benefits and advantages.

SUMMARY

In accordance with a first example, a drug delivery device includes a house, a container, a therapy layer, and a first adhesive. The housing includes a top wall and a bottom wall. The container is at least partially disposed within the housing. The container has an inner volume to contain a drug. The therapy layer has a first side and a second side. The first side faces the bottom wall and the second side faces away from the bottom wall. The first adhesive layer couples the first side of the therapy layer and the bottom wall. The therapy layer is adapted to heat or cool an area adjacent an injection site.

In accordance with a second example, a drug delivery device includes a housing, a container, a therapy layer, and a liner. The housing includes a top wall and a bottom wall. The container is at least partially disposed within the housing. The container has an inner volume containing a drug. The therapy layer has a first side coupled to the bottom wall and a second side including adhesive. The liner covers the adhesive and the second side of the therapy layer. The therapy layer is adapted to generate heat or coldness.

In accordance with a third example, an infusion set includes a needle, a flexible supply tube, a hub, and a heater. The hub has a first end and a second end and a pair of wings extending from sides of the hub. The needle is coupled to the first end of the hub and the flexible supply tube is coupled to the second end of hub. The heater is coupled to the wings and adapted to generate heat at an injection site during a drug delivery process.

In accordance with a fourth example, a drug delivery device includes a housing, a therapy layer, and a liner. The housing carries a delivery member adapted to be inserted into a patient at an injection site. The therapy layer is coupled to the housing. The liner covers the therapy layer. When the liner is removed from the therapy layer, the therapy layer is adapted to heat or cool an area around the injection site.

In further accordance with the foregoing first, second, third, and/or fourth examples, an apparatus may further include any one or more of the following:

In accordance with one example, a second adhesive layer covers at least a portion of the second side of the therapy layer.

In accordance with another example, further including a release liner coupled to the second adhesive layer and covering the therapy layer.

In accordance with another example, the therapy layer defines a needle access port for allowing a needle and/or cannula to pass through the therapy layer.

In accordance with another example, further including a drive mechanism at least partially disposed within the housing. The drive mechanism is adapted to exert a force to urge the drug out of the container.

In accordance with another example, further including a needle, a cannula, and an insertion mechanism at least partially disposed within the housing and operably coupled with the drive mechanism. The insertion mechanism is adapted to insert the needle and the cannula to deliver the drug.

In accordance with another example, the therapy layer includes iron powder, activated carbon, and water.

In accordance with another example, the therapy layer includes iron, sodium chloride, and charcoal.

In accordance with another example, the therapy layer includes iron powder, carbon, one or more metal salts, and water.

In accordance with another example, the one or metal salts is selected from (i) the group consisting of alkali metal salts, alkaline earth metal salts, and mixtures thereof, or (ii) the group consisting of sodium chloride, cupric chloride, and mixtures thereof.

In accordance with another example, the iron powder is selected from the group consisting of cast iron powder, electrolytic iron powder, scrap iron powder, pig iron, wrought iron, various steels, iron alloys, and mixtures thereof.

In accordance with another example, the therapy layer includes an absorbent material.

In accordance with another example, the absorbent material is vermiculite.

In accordance with another example, the therapy layer includes a membrane defining an aeration hole.

In accordance with another example, the therapy layer defines a needle access port for allowing a needle and/or cannula to pass through the therapy layer.

In accordance with another example, further including a needle, a cannula, and an insertion mechanism at least partially disposed within the housing. The insertion mechanism is adapted to insert the needle and the cannula to deliver the drug. The therapy layer defines a needle access port and the needle and the cannula are adapted to pass through the needle access port.

In accordance with another example, the therapy layer includes: (a) iron powder, activated carbon, and water, (b) iron, sodium chloride, and charcoal, or (c) iron powder, carbon, one or more metal salts, and water.

In accordance with another example, the therapy layer includes at least one of (a) an absorbent material and (b) a membrane defining an aeration hole.

In accordance with another example, the delivery member is a needle and the housing includes a hub and a pair of wings extending from the hub and to which the therapy layer is coupled.

In accordance with another example, the housing includes a top wall and a bottom wall and defines an inner volume, and the therapy layer is coupled to the bottom wall.

In accordance with another example, the drug delivery device includes a hand-held, automated injector. The drug delivery device also includes a cap including the liner coupled to the housing.

In accordance with another example, the heater includes a heat therapy adhesive having a removable liner.

BRIEF DESCRIPTION OF THE DRAWINGS

It is believed that the disclosure will be more fully understood from the following description taken in conjunction with the accompanying drawings. Some of the drawings may have been simplified by the omission of selected elements for the purpose of more clearly showing other elements. Such omissions of elements in some drawings are not necessarily indicative of the presence or absence of particular elements in any of the exemplary embodiments, except as may be explicitly delineated in the corresponding written description. Also, none of the drawings is necessarily to scale.

DETAILED DESCRIPTION

The present disclosure generally relates to drug delivery devices having a heating or a cooling device that is used to heat or cool the skin at an injection area prior to and/or during a drug delivery process. Heating the skin may increase blood flow, increase the temperature of the skin, and/or enhance diffusion of the medication within the skin that is being delivered by the drug delivery device. Heating the skin may also reduce pain during drug delivery. Cooling the skin may reduce the temperature of the skin and/or reduce pain during drug delivery.

In some examples, the heating or cooling device is a heat therapy adhesive coupled to the drug delivery device. The heat therapy adhesive may be activated and, thus, begin generating heat when exposed to air and, specifically, when exposed to oxygen. In some examples, when activated, the heat therapy adhesive may generate heat for a relatively long period of time, such as more than one hour and/or for a few hours. The drug delivery device may be a wearable drug delivery device such as an on-body injector, a pen-type injector, or an intravenous (IV) infusion set.

In some examples, the heating or cooling device is a cold pack coupled to the drug delivery device. The cold pack may be activated and, thus, begin cooling when a water packet burst and mixes with a substance within the cold pack. The substance may be Ammonium Nitrate, Ammonium Chloride, and/or Urea. Other substances may prove suitable.

In some examples, the heating and/or cooling device is a topical pain reliever such as a cream, a gel, or other product applied to the skin. The topical pain reliever may be carried by the drug delivery device and may be exposed to skin after a liner covering the topical pain reliever is removed.

Each of the foregoing components of the drug delivery devices will now be described in more detail.

Figure 1:
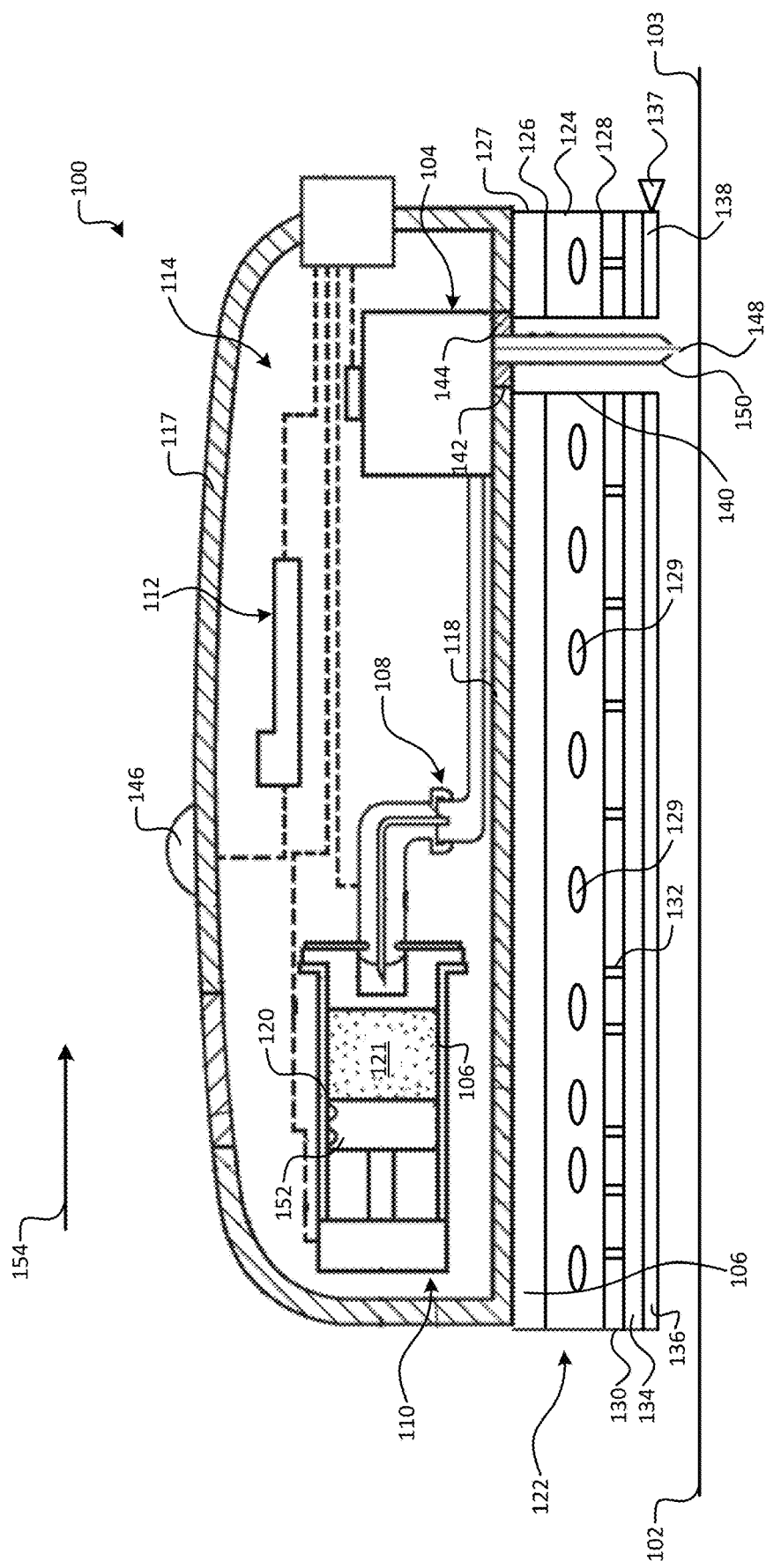
FIG. 1 is a schematic illustration of one embodiment of a drug delivery device constructed in accordance with a first example of the present disclosure.

FIG. 1 is a schematic illustration of one embodiment of a drug delivery device 100 constructed in accordance with a first example of the present disclosure. The drug delivery device 100 may be operated to subcutaneously or transdermally deliver a drug to a patient. In the illustrated embodiment, the drug delivery device 100 is configured as a wearable drug delivery device, such as an on-body injector or an ambulatory infusion pump, and is releasably attachable to an injection site 102 on a patient's tissue 103 (e.g., the patient's skin). In other embodiments, the drug delivery device 100 may be differently configured. For example, the drug delivery device 100 may be configured as an IV infusion set (FIG. 2) or a hand-held, automated injector (FIG. 3). Furthermore, the drug delivery device 100 may be intended for self-administration by the patient, or may be operated by a formally trained healthcare professional or other caregiver to administer the injection.

Generally, the drug delivery device 100 may include an insertion mechanism 104, a container 106, a fluid pathway assembly 108, a drive mechanism 110, and a controller 112, each of which may be disposed within an inner volume 114 of a housing 116. The housing 116 includes a top wall 117 and a bottom wall 118 defining the inner volume 114.

The container 106 has an inner volume 120 that may contain a drug 121. The drug 121 may be referred to as a medication. The drug 121 may be a G-CSF, a pegylated G-CSF, or any other desired pharmaceutical. For example, the pharmaceutical may be an erythropoiesis stimulating agent, a TNF blocker, interleukin receptor specific antibodies, IGF-receptor specific antibodies, or TGF-specific antibodies. Moreover, the drug 22 may be any one of or any combination of the drugs listed below under the heading "Drug Information."

In the example shown, the drug delivery device 100 also includes a heating or cooling device 122. The heating or cooling device 122 may be referred to as a heater. The heating or cooling device 122 includes a therapy layer 124 having a first side 126 facing the bottom wall 118 and a second side 128 facing away from the bottom wall 118. In some examples, the therapy layer 124 is a heat therapy layer or a heat therapy adhesive. In another example, the therapy layer 124 is or includes a cooling pack or a topical pain reliever.

A first adhesive layer 127 is positioned between the first side 126 of the therapy layer 124 and the bottom wall 118 of the housing 116. The first adhesive layer 127 may permanently or otherwise couple the heating or cooling device 122 to the bottom wall 118 of the housing 116. The first adhesive layer 127 may fully cover the bottom wall 118 and/or the first side 126 of the therapy layer 124. Alternatively, the first adhesive layer 127 may partially cover the bottom wall 118 and/or the first side 126 of the therapy layer 124.

In an example, in operation, when the therapy layer 124 is exposed to oxygen, the therapy layer 124 generates heat that may be used to heat the area around the injection site 102. Advantageously, heating the injection site 102 during the drug delivery process may increase blood flow and may enhance diffusion of the drug 121 within the tissue 103. Moreover, heating the injection site 102 may help alleviate pain during drug delivery.

In the example shown, the therapy layer 124 includes a plurality of heat cells 129. The therapy layer 124 and/or the heat cells 129 may be formed using any known methods in the art. For example, the therapy layer 124 and/or the heat cells 129 may include iron, one or more metal salts, carbon, and/or water. The iron may be an iron powder and the carbon may be activated carbon. Some metal salts that may be used include sulfates, chlorides, alkali metal salts, alkaline earth metal salts, sodium chloride, cupric chloride, and/or mixtures thereof. However, other types of salts may prove suitable. The iron may include cast iron powder, electrolytic iron powder, scrap iron powder, pig iron, wrought iron, various steels, iron alloys, and/or mixtures thereof. However, other types of iron and/or metals may prove suitable.

In some examples, the therapy layer 124 and/or the heat cells 129 may include an absorbent material. The absorbent material may be used to hold liquid(s) from a reaction promoter (e.g., the one or metal salts) and/or water that is provided to the iron during, for example, an electrochemical reaction. Some absorbent materials that may be used include, for example, vermiculite, porous silicates, porous materials, wood powder, cotton, and/or paper. However, other absorbent materials may prove suitable.

Still referring to FIG. 1, the therapy layer 124 may be covered by a membrane 130 defining one or more aeration holes 132. The aeration holes 132 may allow the therapy layer 124 and/or the associated heat cells 129 to be exposed to oxygen in a controlled manner such that the temperature produced by the electrochemical reaction does not exceed a threshold level. In some such examples, the membrane 130 may be an air impermeable membrane including the aeration holes 132. In other examples, the membrane 130 may be an air permeable membrane including the aeration holes 132. While the illustrated example includes the membrane 130, in other examples, the membrane 130 may be eliminated.

In the example shown, a second adhesive layer 134 covers at least a portion of the second side 128 of the therapy layer 124. The second adhesive layer 134 may be a patterned adhesive layer such that only a portion of the second side 128 of the therapy layer 124 is covered with the second adhesive layer 134. In another example, the second adhesive layer 134 may cover the entire second side 128 of the therapy layer 124. Regardless, the second adhesive layer 134 may be configured to be releasably attached to the patient's tissue 103 during a drug delivery process. In another example, the therapy layer 124 includes a cold pack or a topical pain reliever. If the therapy layer 124 is a cold pack, the therapy layer 124 may include water and Ammonium Nitrate, Ammonium Chloride, and/or Urea. The water may be stored in a container that is adapted to burst when a threshold amount of force is applied to the container, thereby initiating the chemical reaction. If the therapy layer 124 includes a topical pain reliever, the topical pain reliever may be applied to patient's tissue 103 when the second adhesive layer 134 is attached to the patient's tissue 103.

In some examples, the first adhesive layer 127 is stronger than the second adhesive layer 134 to enable the therapy layer 124 to remain attached to the housing 116 of the drug delivery device 100 when the drug delivery device 100 is detached from the patient's tissue 103. If the second adhesive layer 134 were stronger than the first adhesive layer 127, the therapy layer 124 may inadvertently remain attached to the patient's tissue 103 and detach from the housing 116 of the drug delivery device 100 when attempting to detach the drug delivery device 100 from the patient.

In the example shown, a release liner 136 is coupled to the second adhesive layer 134 and covers the therapy layer 124. The release liner 136 may be adapted to prevent oxygen from accessing the therapy layer 124 and/or the heat cells 129 to substantially ensure an electrochemical reaction does not inadvertently occur. In another example, the release liner 136 covers the topical pain reliever or is omitted (e.g., if the therapy layer 124 is a cold pack).

The release liner 136 may include a release tab 137 that extends from a side 138 of the release liner 136. The release tab 137 may be grasped to detach the release liner 136 from covering the second adhesive layer 134. In some examples, the release liner 136 may include a release coating that faces the second adhesive layer 134 layer to facilitate the removal of the release liner 136 from the second adhesive layer 134.

A needle access port 140 may be defined in the therapy layer 124. An opening 142 may also be defined in the bottom wall 118 of the housing 116. In some examples, a pierceable sterile barrier 144, such as a pierceable septum, may extend across the opening 142 to seal the interior of the housing 116 prior to use. In some embodiments, the pierceable sterile barrier 144 may be omitted, and instead a removable sealing member such as the release liner 136 may cover and seal close the opening 142 prior to use.

An actuator 146 (e.g., a user-depressible button, touchscreen, microphone, etc.) may protrude through or otherwise be disposed at an exterior surface of the housing 116. The actuator 146 may be configured to initiate operation of the drug delivery device 100 by activating, via mechanical and/or electrical means (shown in dotted lines in FIG. 1), the insertion mechanism 104, the fluid pathway assembly 108, the drive mechanism 110, the controller 112, and/or other mechanisms and/or electronics.

In operation, after the release liner 136 is removed initiating the generation of heat or coolness by the heating or cooling device 122 and the second adhesive layer 134 is attached to the patient's tissue 103, the insertion mechanism 104 may be activated to move a delivery member from a retracted position within the housing 116 to a deployed position extending outside of the housing 116. In the example shown, this may include the insertion mechanism 104 inserting a trocar 148 and a hollow cannula 150 surrounding the trocar 148 through the pierceable sterile barrier 144 and into the patient's tissue 103. The cannula 150 may be referred to as a delivery member. Immediately or shortly thereafter, the insertion mechanism 104 may automatically retract the trocar 148, leaving the distal open end of the cannula 150 inside the patient for subcutaneous delivery of the drug 121. The trocar 148 may be solid and have a sharpened end for piercing the patient's skin 103. Furthermore, the trocar 148 may be made of a material that is more rigid than the cannula 150. In some embodiments, the trocar 148 may be made of metal, whereas the cannula 150 may be made of plastic or another polymer. The relative flexibility of the cannula 150 may allow it to be disposed subcutaneously within the patient's tissue 103 for a period of a time without causing pain or significant discomfort to the patient. In other embodiments (not illustrated), the trocar 148 and the cannula 150 may be omitted, and instead the insertion mechanism 104 may insert only a rigid, hollow needle into the patient for subcutaneous delivery of the drug 121.

During operation of the drug delivery device 10, the drive mechanism 110 may push a stopper 152 in a direction generally indicated by arrow 154 within the container 106 in order to expel the drug 121 from the container 106. In some embodiments, the drive mechanism 110 may include one or more springs (e.g., coil springs, torsion springs, etc.) initially retained in an energized state, and which are released upon depression of the actuator 146.

In some examples, the fluid pathway assembly 108 may be configured to establish fluid communication between the container 106 and the insertion mechanism 104 via a sterile fluid flow path during operation of the drug delivery device 100. Prior to use of the drug delivery device 100, the fluid pathway assembly 108 may not be in fluid communication with the container 106. During setup of the drug delivery device 100, or during the initial stages of operation of the drug delivery device 100 prior to drug delivery, the user may manually, or the drug delivery device 100 may automatically, enable, connect, or open the necessary connections to establish fluid communication between the container 106 and the fluid pathway assembly 108. Subsequently, the drive mechanism 110 may move the stopper 152 in the distal direction to force the drug 121 stored in the container 106 through the sterile fluid flow path of the fluid pathway assembly 108 and into the cannula 150 or needle or other delivery member of the insertion mechanism 104 for subcutaneous delivery to the patient.

Where appropriate, any of the above-described sub-assemblies, mechanisms, components, features, functionalities, methods of manufacture, methods of use, and other aspects of the drug delivery device 100 may be replaced with and/or combined with any of the sub-assemblies, mechanisms, components, features, functionalities, methods of manufacture, methods of use, and other aspects of the drug delivery devices described in some or all of the following documents, each of which is hereby incorporated by reference in its entirety for all purposes: U.S. Pat. No. 9,061,097; U.S. Patent Application Publication No. 2017/0124284; U.S. Patent Application Publication No. 2017/0119969; U.S. Patent Application Publication No. 2017/0098058; U.S. Patent Application Publication No. 2017/0124285; U.S. Patent Application Publication No. 2017/0103186; U.S. Provisional Patent Application No. 62/460,501 entitled "INSERTION MECHANISM FOR DRUG DELIVERY DEVICE"; U.S. Provisional Patent Application No. 62/469,226 entitled "INSERTION MECHANISM FOR DRUG DELIVERY DEVICE"; U.S. Provisional Patent Application No. 62/468,190 entitled "INSERTION MECHANISM AND METHOD OF INSERTING A NEEDLE OF A DRUG DELIVERY DEVICE"; U.S. Provisional Patent Application No. 62/460,559 entitled "DRUG DELIVERY DEVICE WITH STERILE FLUID FLOWPATH AND RELATED METHOD OF ASSEMBLY"; U.S. Provisional Patent Application No. 62/294,842 entitled "DRUG DELIVERY DEVICE, METHOD OF MANUFACTURE, AND METHOD OF USE"; U.S. Provisional Patent Application No. 62/297,718 entitled "DRUG DELIVERY DEVICE, METHOD OF MANUFACTURE, AND METHOD OF USE"; U.S. Provisional Patent Application No. 62/320,438 entitled "DRUG DELIVERY DEVICE, METHOD OF MANUFACTURE, AND METHOD OF USE"; International Patent Application No. PCT/US2017/017627 entitled "DRUG DELIVERY DEVICE, METHOD OF MANUFACTURE, AND METHOD OF USE"; and International Patent Application No. PCT/US2017/026524 entitled "DRUG DELIVERY DEVICE, METHOD OF MANUFACTURE, AND METHOD OF USE".

Figure 2:
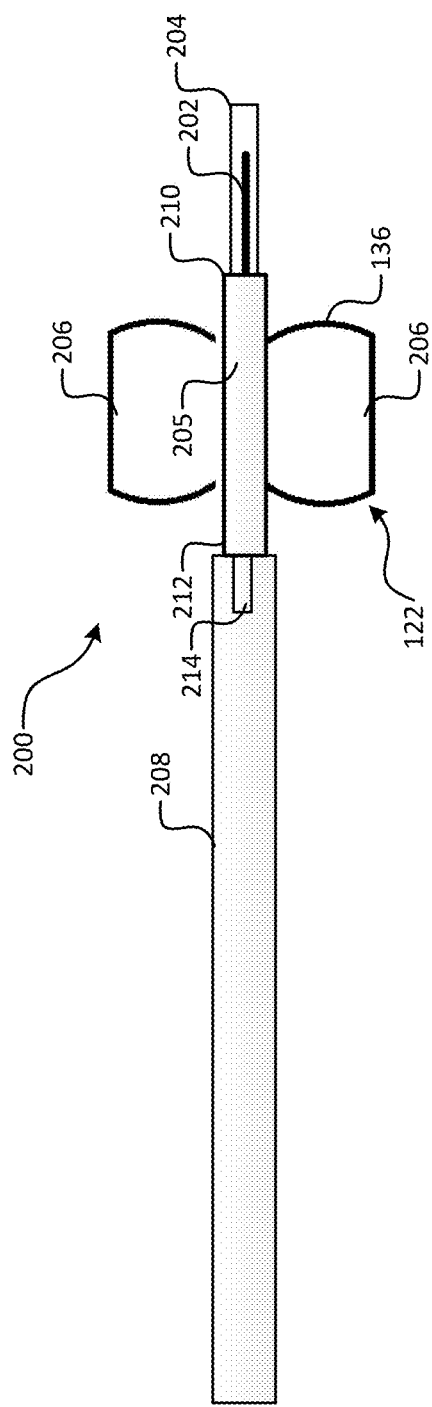
FIG. 2 illustrates is a schematic illustration of another embodiment of a drug delivery device constructed in accordance with a second example of the present disclosure.
Figure 3:
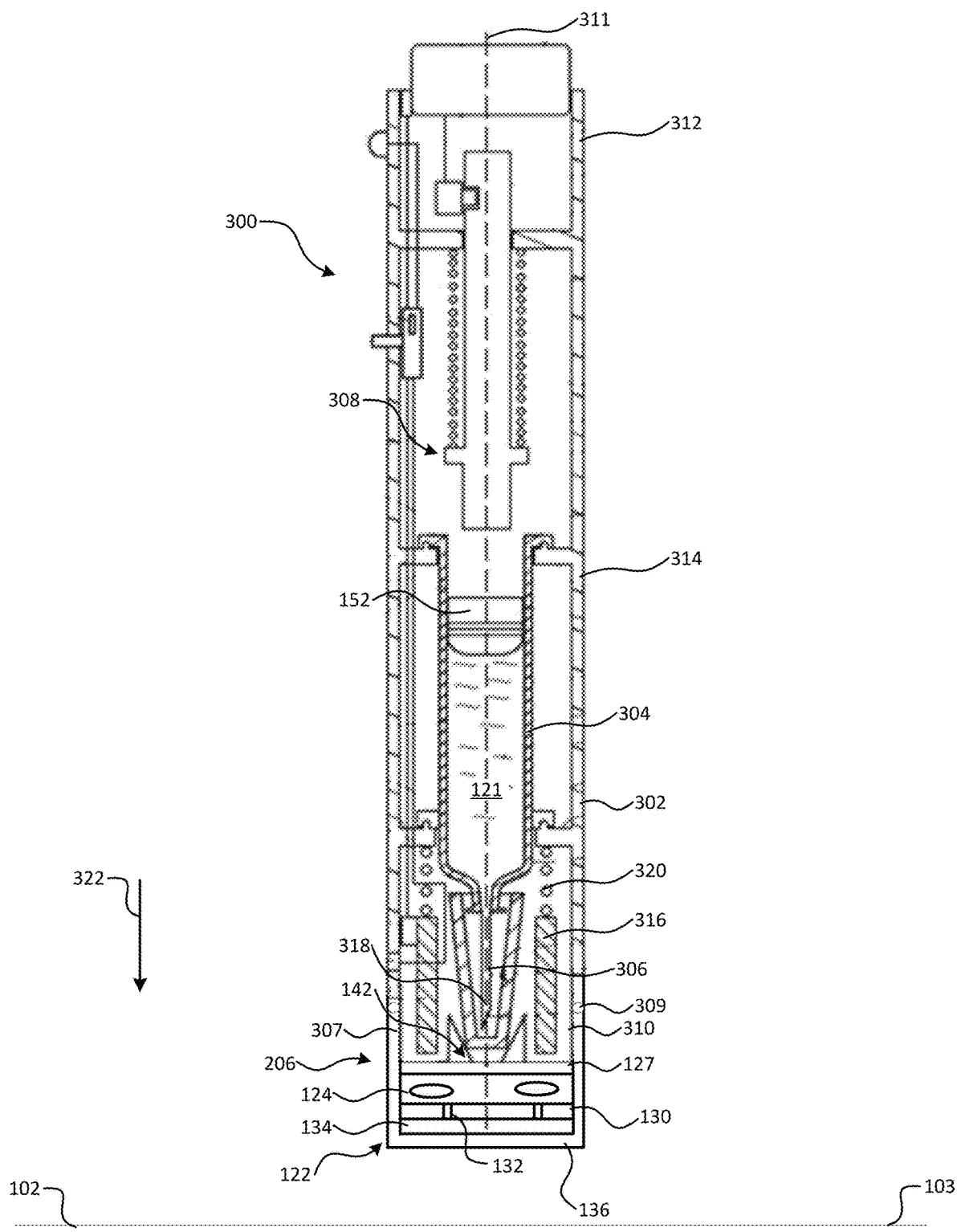
FIG. 3 illustrates is a schematic illustration of another embodiment of a drug delivery device constructed in accordance with a third example of the present disclosure.

FIG. 2 illustrates a schematic partial cross-sectional illustration of another embodiment of a drug delivery device 200 constructed in accordance with a second example of the present disclosure. In the illustrated embodiment, the drug delivery device 200 is configured as an infusion set or a blood collection set, and is releasably attachable to the injection site 102 on the patient's tissue 103 (e.g., the patient's skin).

The drug delivery device 200 includes a needle 202 covered by a removable shield 204, a hub 205 from which a pair of wings 206 extend (one shown in cross-section), and a flexible supply tube 208. The needle 202 may be referred to as a delivery member. The hub 205 may be referred to as a housing. The heating or cooling device 122 is coupled to the wings 206 and is adapted to be releasably attached to the patient's tissue 103 and to heat the injection site 102 prior to and/or during at least a portion of a drug delivery process.

The hub 205 has a first end 210 and a second end 212. The needle 202 is coupled to the first end 210 of the hub 205 and the tube 208 is coupled to the second end 212 of the hub 205.

The needle 202 may be coupled to the hub 205 using adhesive, a fastener, and/or an interference fit. However, other approaches of coupling the needle 202 and the hub 205 may prove suitable.

The hub 205 may include a port 214 extending from the second end 212 that may be inserted into the tube 208 to couple the hub 205 and the tube 208. The coupling between the hub 205 and the tube 108 may form an interference fit. The hub 205 and the tube 208 may be coupled in different ways. For example, the hub 205 and the tube 208 may be coupled using an adhesive or a fastener.

In operation, the shield 204 is removed from the needle 202 and the needle 202 may be inserted into the patient's tissue 103. The heating or cooling device 122 may be activated by removing the release liner 136 to initiate a heating reaction and/or by bursting a water packet to allow the water to mix with a substance to initiate a cooling reaction. In another example, removing the release liner 136 may allow a topical pain reliever to be applied to the patient's tissue 103. The wings 206 may then be coupled adjacent the injection site 102 using the second adhesive layer 134.

FIG. 3 illustrates is a schematic illustration of another embodiment of a drug delivery device 300 constructed in accordance with a third example of the present disclosure. In the illustrated embodiment, the drug delivery device 300 is configured as a hand-held, automated injector for drug delivery, which may be referred to an auto injector.

In the example shown, the drug delivery device 300 includes a housing 302 to which the heating or cooling device 122 is coupled and which houses a container 304 and a needle 306. The needle 306 may be referred to as a delivery member or a syringe. The needle 306 may be movable between a first position in which the needle 306 is housed within the housing 302 and a second position in which the needle 306 extends or at least partially extends from the housing 302 during, for example, an injection procedure. When the needle 306 extends from the housing 302, the needle 306 is in fluid communication with the container 304.

In contrast to the examples disclosed above, in the example shown, the release liner 136 of the heating or cooling device 122 of FIG. 3 is part of a removable cap 307 that covers a distal end 310 of the housing 302. Thus, the coupling between the cap 307 and the housing 302 may deter the heat therapy layer 124 from being exposed to oxygen.

The cap 307 may form a seal such as a hermetic seal with the housing 302. In some examples, a seal 309 is disposed between the cap 307 and the housing 302. The seal 309 may be an O-ring that is received within a groove of one or more of the housing 302 or the cap 307. The cap 307 may be coupled to the housing 302 in different ways. For example, the cap 307 may be coupled to the housing 302 using a snap-fit connection, an interference fit, a frangible, or break-away connection, etc.

In the example shown, a drive mechanism 308 is at least partially disposed within the housing 302 and is adapted to exert a force to urge the drug 121 out of the container 304. In some examples, the drive mechanism 308 may also be adapted to move the needle 306 between the first position within the housing 302 and the second position extending from the housing 302.

Still referring to FIG. 3, the housing 302 may be sized and dimensioned to enable a person to grasp the drug delivery device 300 in a single one of his or her hands. In some embodiments, the housing 302 may be disposable and/or made of a plastic material. The housing 302 may have a generally elongate shape, such as a cylinder, extending along a longitudinal axis 311.

The housing 302 may be a single, unitary component, or, as shown in FIG. 3, defined by multiple interconnected components. In the example shown, a proximal end 312 of the housing 302 is defined by an outer sleeve 314 and the distal end 310 is defined by an inner sleeve 316. The inner sleeve 316 may be slidably disposed within the outer sleeve 314 to provide a deployable guard member for preventing inadvertent contact with a pointed end 318 of the needle 306 before and/or after drug delivery.

A biasing member 320 such as a spring may be included for urging the inner sleeve 316 toward the deployed position. A biasing force generated by the biasing member 49 may be overcome by pressing the inner sleeve 48 against the patient's tissue 103 at the injection site 102, for example.

In operation, the cap 307 may be removed from the housing 302, thereby activating the heating or cooling device 122. Thereafter, the distal end 316 of the housing 302 may be pressed against the injection site 102. A force may be applied to the proximal end 312 of the housing 302 in a direction generally indicated by arrow 322 to urge the needle 306 into the second position and/or to urge the drug 121 to dispense out of the needle 306 and into the patient.

Drug Information

The present disclosure describes various devices, assemblies, components, subsystems and methods for use related to a drug delivery device. The devices, assemblies, components, subsystems, methods or drug delivery devices can further comprise or be used with a drug including but not limited to those drugs identified below as well as their generic and biosimilar counterparts. The term drug, as used herein, can be used interchangeably with other similar terms and can be used to refer to any type of medicament or therapeutic material including traditional and non-traditional pharmaceuticals, nutraceuticals, supplements, biologics, biologically active agents and compositions, large molecules, biosimilars, bioequivalents, therapeutic antibodies, polypeptides, proteins, small molecules and generics. Non-therapeutic injectable materials are also encompassed. The drug may be in liquid form, a lyophilized form, or in a reconstituted from lyophilized form. The following example list of drugs should not be considered as all-inclusive or limiting.

The drug will be contained in a reservoir. In some instances, the reservoir is a primary container that is either filled or pre-filled for treatment with the drug. The primary container can be a vial, a cartridge or a pre-filled syringe.

In some embodiments, the reservoir of the drug delivery device may be filled with or the device can be used with colony stimulating factors, such as granulocyte colony-stimulating factor (G-CSF). Such G-CSF agents include but are not limited to Neulasta® (pegfilgrastim, pegylated filgastrim, pegylated G-CSF, pegylated hu-Met-G-CSF) and Neupogen® (filgrastim, G-CSF, hu-MetG-CSF), UDENYCA® (pegfilgrastim-cbqv), Ziextenzo® (LA-EP2006; pegfilgrastim-bmez), or FULPHILA (pegfilgrastim-bmez).

In other embodiments, the drug delivery device may contain or be used with an erythropoiesis stimulating agent (ESA), which may be in liquid or lyophilized form. An ESA is any molecule that stimulates erythropoiesis. In some embodiments, an ESA is an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin iota, epoetin omega, epoetin delta, epoetin zeta, epoetin theta, and epoetin delta, pegylated erythropoietin, carbamylated erythropoietin, as well as the molecules or variants or analogs thereof.

Among particular illustrative proteins are the specific proteins set forth below, including fusions, fragments, analogs, variants or derivatives thereof: OPGL specific antibodies, peptibodies, related proteins, and the like (also referred to as RANKL specific antibodies, peptibodies and the like), including fully humanized and human OPGL specific antibodies, particularly fully humanized monoclonal antibodies; Myostatin binding proteins, peptibodies, related proteins, and the like, including myostatin specific peptibodies; IL-4 receptor specific antibodies, peptibodies, related proteins, and the like, particularly those that inhibit activities mediated by binding of IL-4 and/or IL-13 to the receptor; Interleukin 1-receptor 1 ("ID-R1") specific antibodies, peptibodies, related proteins, and the like; Ang2 specific antibodies, peptibodies, related proteins, and the like; NGF specific antibodies, peptibodies, related proteins, and the like; CD22 specific antibodies, peptibodies, related proteins, and the like, particularly human CD22 specific antibodies, such as but not limited to humanized and fully human antibodies, including but not limited to humanized and fully human monoclonal antibodies, particularly including but not limited to human CD22 specific IgG antibodies, such as, a dimer of a human-mouse monoclonal hLL2 gamma-chain disulfide linked to a human-mouse monoclonal hLL2 kappa-chain, for example, the human CD22 specific fully humanized antibody in Epratuzumab, CAS registry number 501423-23-0; IGF-1 receptor specific antibodies, peptibodies, and related proteins, and the like including but not limited to anti-IGF-1R antibodies; B-7 related protein 1 specific antibodies, peptibodies, related proteins and the like ("B7RP-1" and also referring to B7H2, ICOSL, B7h, and CD275), including but not limited to B7RP-specific fully human monoclonal IgG2 antibodies, including but not limited to fully human IgG2 monoclonal antibody that binds an epitope in the first immunoglobulin-like domain of B7RP-1, including but not limited to those that inhibit the interaction of B7RP-1 with its natural receptor, ICOS, on activated T cells; IL-15 specific antibodies, peptibodies, related proteins, and the like, such as, in particular, humanized monoclonal antibodies, including but not limited to HuMax IL-15 antibodies and related proteins, such as, for instance, 145c7; IFN gamma specific antibodies, peptibodies, related proteins and the like, including but not limited to human IFN gamma specific antibodies, and including but not limited to fully human anti-IFN gamma antibodies; TALL-1 specific antibodies, peptibodies, related proteins, and the like, and other TALL specific binding proteins; Parathyroid hormone ("PTH") specific antibodies, peptibodies, related proteins, and the like; Thrombopoietin receptor ("TPO-R") specific antibodies, peptibodies, related proteins, and the like; Hepatocyte growth factor ("HGF") specific antibodies, peptibodies, related proteins, and the like, including those that target the HGF/SF:cMet axis (HGF/SF:c-Met), such as fully human monoclonal antibodies that neutralize hepatocyte growth factor/scatter (HGF/SF); TRAIL-R2 specific antibodies, peptibodies, related proteins and the like; Activin A specific antibodies, peptibodies, proteins, and the like; TGF-beta specific antibodies, peptibodies, related proteins, and the like; Amyloid-beta protein specific antibodies, peptibodies, related proteins, and the like; c-Kit specific antibodies, peptibodies, related proteins, and the like, including but not limited to proteins that bind c-Kit and/or other stem cell factor receptors; OX40L specific antibodies, peptibodies, related proteins, and the like, including but not limited to proteins that bind OX40L and/or other ligands of the OX40 receptor; Activase® (alteplase, tPA); Aranesp® (darbepoetin alfa) Erythropoietin [30-asparagine, 32-threonine, 87-valine, 88-asparagine, 90-threonine], Darbepoetin alfa, novel erythropoiesis stimulating protein (NESP); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-?4β7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Kanjinti™ (trastuzumab-anns) anti-HER2 monoclonal antibody, biosimilar to Herceptin®, or another product containing trastuzumab for the treatment of breast or gastric cancers; Humatrope® (somatropin, Human Growth Hormone); Humira® (adalimumab); Vectibix® (panitumumab), Xgeva® (denosumab), Prolia® (denosumab), Immunoglobulin G2 Human Monoclonal Antibody to RANK Ligand, Enbrel® (etanercept, TNF-receptor/Fc fusion protein, TNF blocker), Nplate® (romiplostim), rilotumumab, ganitumab, conatumumab, brodalumab, insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Solids™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Orthoclone OKT3® (muromonab-CD3, anti-CD3 monoclonal antibody); Procrit® (epoetin alfa); Remicade® (infliximab, anti-TNF? monoclonal antibody); Reopro® (abciximab, anti-GP IIb/IIIa receptor monoclonal antibody); Actemra® (anti-IL6 Receptor mAb); Avastin® (bevacizumab), HuMax-CD4 (zanolimumab); Mvasi™ (bevacizumab-awwb); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 145c7-CHO (anti-IL15 antibody, see U.S. Pat. No. 7,153,507); Tysabri® (natalizumab, anti-?4integrin mAb); Valortim® (MDX-1303, anti-*B. anthracis* protective antigen mAb); ABthrax™; Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2R? mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNF? mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-?5?1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxinl mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFN? mAb (MEDI-545, MDX-198); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-I P10 Ulcerative Colitis mAb (MDX-1100); BMS-66513; anti-Mannose Receptor/hCG? mAb (MDX-1307); anti-mesothelin dsFv-PE38 conjugate (CAT-5001); anti-PD1mAb (MDX-1106 (ONO-4538)); anti-PDGFR? antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; and anti-ZP3 mAb (HuMax-ZP3).

In some embodiments, the drug delivery device may contain or be used with a sclerostin antibody, such as but not limited to romosozumab, blosozumab, BPS 804 (Novartis), Evenity™ (romosozumab-aqqg), another product containing romosozumab for treatment of postmenopausal osteoporosis and/or fracture healing and in other embodiments, a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab). In other embodiments, the drug delivery device may contain or be used with rilotumumab, bixalomer, trebananib, ganitumab, conatumumab, motesanib diphosphate, brodalumab, vidupiprant or panitumumab. In some embodiments, the reservoir of the drug delivery device may be filled with or the device can be used with IMLYGIC® (talimogene laherparepvec) or another oncolytic HSV for the treatment of melanoma or other cancers including but are not limited to OncoVEXGALV/CD; OrienX010; G207, 1716; NV1020; NV12023; NV1034; and NV1042. In some embodiments, the drug delivery device may contain or be used with endogenous tissue inhibitors of metalloproteinases (TIMPs) such as but not limited to TIMP-3. In some embodiments, the drug delivery device may contain or be used with Aimovig® (erenumab-aooe), anti-human CGRP-R (calcitonin gene-related peptide type 1 receptor) or another product containing erenumab for the treatment of migraine headaches. Antagonistic antibodies for human calcitonin gene-related peptide (CGRP) receptor such as but not limited to erenumab and bispecific antibody molecules that target the CGRP receptor and other headache targets may also be delivered with a drug delivery device of the present disclosure. Additionally, bispecific T cell engager (BITE®) antibodies such as but not limited to BLINCYTO® (blinatumomab) can be used in or with the drug delivery device of the present disclosure. In some embodiments, the drug delivery device may contain or be used with an APJ large molecule agonist such as but not limited to apelin or analogues thereof. In some embodiments, a therapeutically effective amount of an anti-thymic stromal lymphopoietin (TSLP) or TSLP receptor antibody is used in or with the drug delivery device of the present disclosure. In some embodiments, the drug delivery device may contain or be used with Avsola™ (infliximab-axxq), anti-TNF? monoclonal antibody, biosimilar to Remicade® (infliximab) (Janssen Biotech, Inc.) or another product containing infliximab for the treatment of autoimmune diseases. In some embodiments, the drug delivery device may contain or be used with Kyprolis® (carfilzomib), (2S)—N—((S)-1-((S)-4-methyl-1-((R)-2-methyloxiran-2-yl)-1-oxopentan-2-ylcarbamoyl)-2-phenylethyl)-2-((S)-2-(2-morpholinoacetamido)-4-phenylbutanamido)-4-methylpentanamide, or another product containing carfilzomib for the treatment of multiple myeloma. In some embodiments, the drug delivery device may contain or be used with Otezla® (apremilast), N-[2-[(1S)-1-(3-ethoxy-4-methoxyphenyl)-2-(methylsulfonyl) ethyl]-2,3-dihydro-1,3-dioxo-1H-isoindol-4-yl]acetamide, or another product containing apremilast for the treatment of various inflammatory diseases. In some embodiments, the drug delivery device may contain or be used with Parsabiv™ (etelcalcetide HCl, KAI-4169) or another product containing etelcalcetide HCl for the treatment of secondary hyperparathyroidism (sHPT) such as in patients with chronic kidney disease (KD) on hemodialysis. In some embodiments, the drug delivery device may contain or be used with ABP 798 (rituximab), a biosimilar candidate to Rituxan®/ MabThera™, or another product containing an anti-CD20 monoclonal antibody. In some embodiments, the drug delivery device may contain or be used with a VEGF antagonist such as a non-antibody VEGF antagonist and/or a VEGF-Trap such as aflibercept (Ig domain 2 from VEGFR1 and Ig domain 3 from VEGFR2, fused to Fc domain of IgG1). In some embodiments, the drug delivery device may contain or be used with ABP 959 (eculizumab), a biosimilar candidate to Soliris®, or another product containing a monoclonal antibody that specifically binds to the complement protein C5. In some embodiments, the drug delivery device may contain or be used with Rozibafusp alfa (formerly AMG 570) is a novel bispecific antibody-peptide conjugate that simultaneously blocks ICOSL and BAFF activity. In some embodiments, the drug delivery device may contain or be used with Omecamtiv mecarbil, a small molecule selective cardiac myosin activator, or myotrope, which directly targets the contractile mechanisms of the heart, or another product containing a small molecule selective cardiac myosin activator. In some embodiments, the drug delivery device may contain or be used with Sotorasib (formerly known as AMG 510), a KRASG12C small molecule inhibitor, or another product containing a KRASG12C small molecule inhibitor. In some embodiments, the drug delivery device may contain or be used with Tezepelumab, a human monoclonal antibody that inhibits the action of thymic stromal lymphopoietin (TSLP), or another product containing a human monoclonal antibody that inhibits the action of TSLP. In some embodiments, the drug delivery device may contain or be used with AMG 714, a human monoclonal antibody that binds to Interleukin-15 (IL-15) or another product containing a human monoclonal antibody that binds to Interleukin-15 (IL-15). In some embodiments, the drug delivery device may contain or be used with AMG 890, a small interfering RNA (siRNA) that lowers lipoprotein(a), also known as Lp(a), or another product containing a small interfering RNA (siRNA) that lowers lipoprotein(a). In some embodiments, the drug delivery device may contain or be used with ABP 654 (human IgG1 kappa antibody), a biosimilar candidate to Stelara®, or another product that contains human IgG1 kappa antibody and/or binds to the p40 subunit of human cytokines interleukin (IL)-12 and IL-23. In some embodiments, the drug delivery device may contain or be used with Amjevita™ or Amgevita™ (formerly ABP 501) (mab anti-TNF human IgG1), a biosimilar candidate to Humira®, or another product that contains human mab anti-TNF human IgG1. In some embodiments, the drug delivery device may contain or be used with AMG 160, or another product that contains a half-life extended (HLE) anti-prostate-specific membrane antigen (PSMA)× anti-CD3 BiTE® (bispecific T cell engager) construct. In some embodiments, the drug delivery device may contain or be used with AMG 119, or another product containing a delta-like ligand 3 (DLL3) CAR T (chimeric antigen receptor T cell) cellular therapy. In some embodiments, the drug delivery device may contain or be used with AMG 119, or another product containing a delta-like ligand 3 (DLL3) CART (chimeric antigen receptor T cell) cellular therapy. In some embodiments, the drug delivery device may contain or be used with AMG 133, or another product containing a gastric inhibitory polypeptide receptor (GIPR) antagonist and GLP-1R agonist. In some embodiments, the drug delivery device may contain or be used with AMG 171 or another product containing a Growth Differential Factor 15 (GDF15) analog. In some embodiments, the drug delivery device may contain or be used with AMG 176 or another product containing a small molecule inhibitor of myeloid cell leukemia 1 (MCL-1). In some embodiments, the drug delivery device may contain or be used with AMG 199 or another product containing a half-life extended (HLE) bispecific T cell engager construct (BiTE®). In some embodiments, the drug delivery device may contain or be used with AMG 256 or another product containing an anti-PD-1× IL21 mutein and/or an IL-21 receptor agonist designed to selectively turn on the Interleukin 21 (IL-21) pathway in programmed cell death-1 (PD-1) positive cells. In some embodiments, the drug delivery device may contain or be used with AMG 330 or another product containing an anti-CD33× anti-CD3 BiTE® (bispecific T cell engager) construct. In some embodiments, the drug delivery device may contain or be used with AMG 404 or another product containing a human anti-programmed cell death-1 (PD-1) monoclonal antibody being investigated as a treatment for patients with solid tumors. In some embodiments, the drug delivery device may contain or be used with AMG 427 or another product containing a half-life extended (HLE) anti-fms-like tyrosine kinase 3 (FLT3)× anti-CD3 BiTE® (bispecific T cell engager) construct. In some embodiments, the drug delivery device may contain or be used with AMG 430 or another product containing an anti-Jagged-1 monoclonal antibody. In some embodiments, the drug delivery device may contain or be used with AMG 506 or another product containing a multi-specific FAPx4-1BB-targeting DARPin® biologic under investigation as a treatment for solid tumors. In some embodiments, the drug delivery device may contain or be used with AMG 509 or another product containing a bivalent T-cell engager and is designed using XmAb® 2+1 technology. In some embodiments, the drug delivery device may contain or be used with AMG 562 or another product containing a half-life extended (HLE) CD19× CD3 BiTE® (bispecific T cell engager) construct. In some embodiments, the drug delivery device may contain or be used with Efavaleukin alfa (formerly AMG 592) or another product containing an IL-2 mutein Fc fusion protein. In some embodiments, the drug delivery device may contain or be used with AMG 596 or another product containing a CD3× epidermal growth factor receptor vlll (EGFRvIII) BiTE® (bispecific T cell engager) molecule. In some embodiments, the drug delivery device may contain or be used with AMG 673 or another product containing a half-life extended (HLE) anti-CD33× anti-CD3 BiTE® (bispecific T cell engager) construct. In some embodiments, the drug delivery device may contain or be used with AMG 701 or another product containing a half-life extended (HLE) anti-B-cell maturation antigen (BCMA)× anti-CD3 BiTE® (bispecific T cell engager) construct. In some embodiments, the drug delivery device may contain or be used with AMG 757 or another product containing a half-life extended (HLE) anti-delta-like ligand 3 (DLL3)× anti-CD3 BiTE® (bispecific T cell engager) construct. In some embodiments, the drug delivery device may contain or be used with AMG 910 or another product containing a half-life extended (HLE) epithelial cell tight junction protein claudin 18.2× CD3 BiTE® (bispecific T cell engager) construct.

Although the drug delivery devices, assemblies, components, subsystems and methods have been described in terms of exemplary embodiments, they are not limited thereto. The detailed description is to be construed as exemplary only and does not describe every possible embodiment of the present disclosure. Numerous alternative embodiments could be implemented, using either current technology or technology developed after the filing date of this patent that would still fall within the scope of the claims defining the invention(s) disclosed herein.

Those skilled in the art will recognize that a wide variety of modifications, alterations, and combinations can be made with respect to the above described embodiments without departing from the spirit and scope of the invention(s) disclosed herein, and that such modifications, alterations, and combinations are to be viewed as being within the ambit of the inventive concept(s).

What is claimed is:

1. A drug delivery device comprising:
   a housing including a top wall and a bottom wall;
   a container at least partially disposed within the housing, the container having an inner volume to contain a drug;
   a therapy layer having a first side and a second side, the first side facing the bottom wall and the second side facing away from the bottom wall; and
   a first adhesive layer coupling the first side of the therapy layer and the bottom wall, the first adhesive layer substantially covering the bottom wall and the first side of the therapy layer,
      wherein the therapy layer is adapted to at least one of heat or cool an area adjacent to an injection site.

2. The drug delivery device of claim 1, further comprising a second adhesive layer covering at least a portion of the second side of the therapy layer.

3. The drug delivery device of claim 2, further comprising a release liner coupled to the second adhesive layer and covering the therapy layer.

4. The drug delivery device of claim 1, wherein the therapy layer defines a needle access port for allowing a needle and/or cannula to pass through the therapy layer.

5. The drug delivery device of claim 1, further comprising a drive mechanism at least partially disposed within the housing, the drive mechanism adapted to exert a force to urge the drug out of the container.

6. The drug delivery device of claim 5, further comprising a needle, a cannula, and an insertion mechanism at least partially disposed within the housing and operably coupled with the drive mechanism, the insertion mechanism adapted to insert the needle and the cannula to deliver the drug.

7. The drug delivery device of claim 1, wherein the therapy layer comprises:
   (a) iron powder, activated carbon, and water,
   (b) iron, sodium chloride, and charcoal, or
   (c) iron powder, carbon, one or more metal salts, and water.

8. The drug delivery device of claim 7, wherein the therapy layer comprises (c) and the one or metal salts is selected from (i) the group consisting of alkali metal salts, alkaline earth metal salts, and mixtures thereof, or (ii) the group consisting of sodium chloride, cupric chloride, and mixtures thereof.

9. The drug delivery device of claim 7, wherein the iron powder is selected from the group consisting of cast iron powder, electrolytic iron powder, scrap iron powder, pig iron, wrought iron, various steels, iron alloys, and mixtures thereof.

10. The drug delivery device of claim 1, wherein the therapy layer comprises an absorbent material.

11. The drug delivery device of claim 10, wherein the absorbent material comprises vermiculite.

12. The drug delivery device of claim 1, wherein the therapy layer comprises a membrane defining an aeration hole.

13. A drug delivery device comprising:
    a housing including a top wall and a bottom wall;
    a container at least partially disposed within the housing, the container having an inner volume containing a drug;
    a therapy layer having a first side including first adhesive coupled to the bottom wall by the first adhesive and a second side including second adhesive; and
    a liner covering the second adhesive and the second side of the therapy layer,
       wherein the therapy layer is adapted to generate heat or coldness.

14. The drug delivery device of claim 13, wherein the therapy layer defines a needle access port for allowing a needle and/or cannula to pass through the therapy layer.

15. The drug delivery device of claim 13, further comprising a needle, a cannula, and an insertion mechanism at least partially disposed within the housing, the insertion mechanism adapted to insert the needle and the cannula to deliver the drug, wherein the therapy layer defines a needle access port and the needle and the cannula are adapted to pass through the needle access port.

16. The drug delivery device of claim 13, wherein the therapy layer comprises:
   (a) iron powder, activated carbon, and water, (b) iron, sodium chloride, and charcoal, or
   (c) iron powder, carbon, one or more metal salts, and water.

17. The drug delivery device of claim 16, wherein the therapy layer comprises (c) and the one or metal salts is selected from (i) the group consisting of alkali metal salts, alkaline earth metal salts, and mixtures thereof, or (ii) the group consisting of sodium chloride, cupric chloride, and mixtures thereof.

18. The drug delivery device of claim 13, wherein the therapy layer comprises at least one of (a) an absorbent material and (b) a membrane defining an aeration hole.

19. An infusion set comprising:
   a needle;
   a flexible supply tube;
   a hub having a first end and a second end and having a pair of wings extending from sides of the hub, the needle being coupled to the first end of the hub and the flexible supply tube being coupled to the second end of hub; and
   a heater coupled to the wings and adapted to generate heat at an injection site during a drug delivery process.

20. The infusion set of claim 19, wherein the heater comprises a heat therapy adhesive having a removable liner.

* * * * *